(12) United States Patent
Kirsch et al.

(10) Patent No.: US 6,990,427 B2
(45) Date of Patent: *Jan. 24, 2006

(54) GAIN FACTOR AND POSITION DETERMINATION SYSTEM

(75) Inventors: Stefan R. Kirsch, Lauchringen (DE); Hans R. Schild, Uetikon am See (CH); Christian J. Schilling, Wuerenlingen (DE)

(73) Assignee: Northern Digital Inc., Waterloo ( * ) Notice: Subject to any disclaimer, the term of this patent is extended or adjusted under 35 U.S.C. 154(b) by 0 days.

This patent is subject to a terminal disclaimer.

(21) Appl. No.: 10/624,917

(22) Filed: Jul. 22, 2003

(65) Prior Publication Data

US 2005/0049820 A1 Mar. 3, 2005

Related U.S. Application Data

(63) Continuation of application No. 09/892,153, filed on Jun. 26, 2001, now Pat. No. 6,625,563.

(51) Int. Cl.
*G06F 15/00* (2006.01)

(52) U.S. Cl. .................. 702/150; 702/152; 702/153

(58) Field of Classification Search .............. 702/150, 702/151, 152, 153, 154; 600/229, 230, 407, 600/424; 324/207.12–207.17, 318, 322; 606/108, 130
See application file for complete search history.

(56) References Cited

U.S. PATENT DOCUMENTS

| | | | |
|---|---|---|---|
| 5,392,210 A | 2/1995 | Scholz | |
| 5,457,641 A | 10/1995 | Zimmer et al. | |
| 5,592,939 A | 1/1997 | Martinelli | |
| 5,645,065 A * | 7/1997 | Shapiro et al. | ............. 600/424 |
| 5,747,996 A | 5/1998 | Fuchs | |
| 5,762,064 A | 6/1998 | Polvani | |
| 5,767,669 A | 6/1998 | Hansen et al. | |
| 5,879,297 A | 3/1999 | Haynor et al. | |
| 5,913,820 A | 6/1999 | Bladen et al. | |
| 6,073,043 A | 6/2000 | Schneider | |
| 6,097,190 A | 8/2000 | Foerster | |
| 6,226,547 B1 * | 5/2001 | Lockhart et al. | ............. 600/424 |

(Continued)

FOREIGN PATENT DOCUMENTS

| | | |
|---|---|---|
| GB | 2331807 A | 2/1999 |
| WO | WO 97/36192 | 3/1997 |

OTHER PUBLICATIONS

Borse, G.J., "Numerical Methods with Matlab: A Resource for Scientists and Engineers", 1997, PWS Publishing Company, pp. 313–316.

(Continued)

*Primary Examiner*—Bryan Bui
(74) *Attorney, Agent, or Firm*—Fish & Richardson P.C.

(57) ABSTRACT

A system for determining the position, orientation and system gain factor of a probe includes a plurality of magnetic field sources and at least one magnetic field sensor, such that a combination of a magnetic field sensor and a magnetic field source generates a unique measured magnetic field value. The system includes a probe whose gain, position, and orientation affect these unique measured magnetic field values. A processor is configured to receive and iteratively process these unique measured magnetic field values to determine a system gain factor indicative of the gain of the probe and a plurality of location factors indicative of the position and orientation of the probe. The number of unique measured magnetic field values generated must be at least equal to the sum of the number of gain and location factors calculated.

22 Claims, 8 Drawing Sheets

U.S. PATENT DOCUMENTS

| | | |
|---|---|---|
| 6,266,551 B1 | 7/2001 | Osadchy et al. |
| 6,427,079 B1 | 7/2002 | Schneider et al. |
| 6,625,563 B2 * | 9/2003 | Kirsch et al. ............... 702/150 |
| 2002/0065455 A1 | 5/2002 | Ben-Haim et al. |

OTHER PUBLICATIONS

European Examination Report dated Jan. 31, 2005 for EP Application No. 02740177.7.

* cited by examiner

GAIN FACTOR AND POSITION DETERMINATION SYSTEM

CROSS REFERENCE TO RELATED APPLICATIONS

This application is a continuation of U.S. application Ser. No. 09/892,153, filed Jun. 26, 2001 now U.S. Pat. No. 6,625,563. The content of the prior application is incorporated herein by reference in its entirety.

TECHNICAL FIELD

This invention relates to systems that use magnetic fields to determine an object's location and orientation, and system gain factor.

BACKGROUND

As is known in the art, systems may use magnetic field measurements to indirectly determine the location and orientation of an object. These systems are useful, for example, in the medical field, because they are able to accurately locate an object in a patient's body with only minimal intrusion into the body. The intrusion involves placing a small probe near the object to be located. The three-dimensional location and orientation of the probe is then determined from the effect that the probe's location and orientation have on magnetic field measurements.

The probe may be either a source or a sensor of a magnetic field. If the probe is a source, sensors exterior to the body measure the field produced by the probe. If the probe is a sensor, magnetic sources exterior to the body produce the fields being measured.

Determining a probe's location and orientation from magnetic field measurements is not straight forward because the measured magnetic fields are nonlinear functions of the location and orientation. To determine the probe's location and orientation from the measured magnetic field values, the probe's location and orientation are first presumed or "guessed" to be at a predicted location and orientation. An iterative process is used to compare values of the magnetic field at the guessed probe location and orientation with the measured field values. If the magnetic field values at a guessed location and orientation are close to the measured values, the guessed location and orientation are presumed to accurately represent the actual location and orientation of the probe.

The iterative process uses a physical model for the probe's environment. The physical model specifies the location and orientation of each field source. From the specified locations and orientations, laws of electrodynamics determine the field values.

As the probe and its positioning system are physical systems, they are susceptible to various external influences (e.g., stray magnetic fields, field absorbing materials being positioned proximate the field generators and/or sensors, etc.) that affect the gain of the system. Additionally, these physical devices have various engineering tolerances (e.g., cable resistance, probe gain, input impedance, etc.) that also affect overall system gain. Accordingly, each time a component of the system is replaced, the system must be manually recalibrated.

SUMMARY

According to an aspect of this invention, a system for determining the position, orientation and system gain factor of a probe includes magnetic field sources and at least one magnetic field sensor, such that a combination of a magnetic field sensor and a magnetic field source generates a unique measured magnetic field value. The system also includes a probe whose position and orientation affect the unique measured magnetic field values. A processor, coupled to receive these unique measured magnetic field values, iteratively processes measured magnetic field values to determine a system gain factor indicative of the gain of the probe and location factors indicative of the position and orientation of the probe. The number of unique measured magnetic field values generated must be at least equal to the sum of the number of factors calculated.

One or more of the following features may also be included. The iterative process is configured to determine a function of the differences between the measured magnetic field values and a plurality of predicted magnetic field values. The processor includes a calculated location process for calculating the predicted magnetic field values, in that the calculated location process guesses an initial gain, position and orientation for the probe, and then calculates the predicted magnetic field values based on a physical model and the initial gain, position and orientation. The initial position and orientation may be a predetermined or randomly selected fixed point.

The processor includes an optimization function for determining an extremum indicative of the differences between the measured magnetic field values and the predicted magnetic field values. The optimization function is a least squares sum function. The processor includes a repositioning process for adjusting the initial gain, position and orientation of the probe in response to the extremum being in a predefined range of unacceptable values, which is indicative of an unacceptable level of difference between the measured magnetic field values and the plurality of predicted magnetic field values. The location factors may include spatial, spherical, and/or rotational coordinates.

According to a further aspect of this invention, a method for determining the position, orientation and system gain factor of a three-dimensional object includes positioning a plurality of magnetic field sources proximate the three-dimensional object and positioning at least one magnetic field sensor in a fixed spatial relationship with that three-dimensional object. A combination of a magnetic field sensor and a magnetic field source generates a unique measured magnetic field value. Further, the position and orientation of the three-dimensional object affects these unique measured magnetic field values. The method determines a system gain factor indicative of the gain of the three-dimensional object and a plurality of location factors indicative of the position and orientation of the three-dimensional object. The number of unique measured magnetic field values generated must be at least equal to the sum of the number of factors calculated.

One or more of the following features may also be included. The step of determining a system gain factor and a plurality of location factors includes determining a function of the differences between the measured magnetic field values and a plurality of predicted magnetic field values. The step of determining a system gain factor and a plurality of location factors includes guessing an initial gain, position and orientation for the three-dimensional object and calculating the predicted magnetic field values based on a physical model and the initial gain, position and orientation. The step of determining a system gain factor and a plurality of location factors includes determining an extremum indicative of the differences between the measured magnetic field values and the predicted magnetic field values. The step of determining a system gain factor and a plurality of location factors includes adjusting the initial gain, position, and orientation of the three-dimensional object in response to the extremum being in a predefined range of unacceptable values, which is indicative of an unacceptable level of difference between the measured magnetic field values and the plurality of predicted magnetic field values.

While the system and method described above includes a plurality of magnetic field sources and at least one magnetic field sensor, the system can also include a plurality of magnetic field sensors and at least one magnetic field source. Further, while the system and method described above were said to include a probe, that probe can actually be any three-dimensional object, such as a hollow tube (e.g., a biopsy needle).

The advantages of the above aspects of the invention are numerous. As this system automatically calculates the system gain factor for the probe or three-dimensional object being utilized, device gain calibration is automated. Therefore, the need for tedious and time-consuming manual gain recalibration is eliminated. Additionally, as this calibration process is automated, the system components (e.g., probes, sensors, leads, etc.) can be quickly and easily swapped and the system reconfigured without the need for manual gain recalibration. This, in turn, streamlines and simplifies the reconfiguration process. Additionally, as the system automatically and continuously determines the system gain factor, the system can be physically moved without fear of external influences mandating manual gain recalibration.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
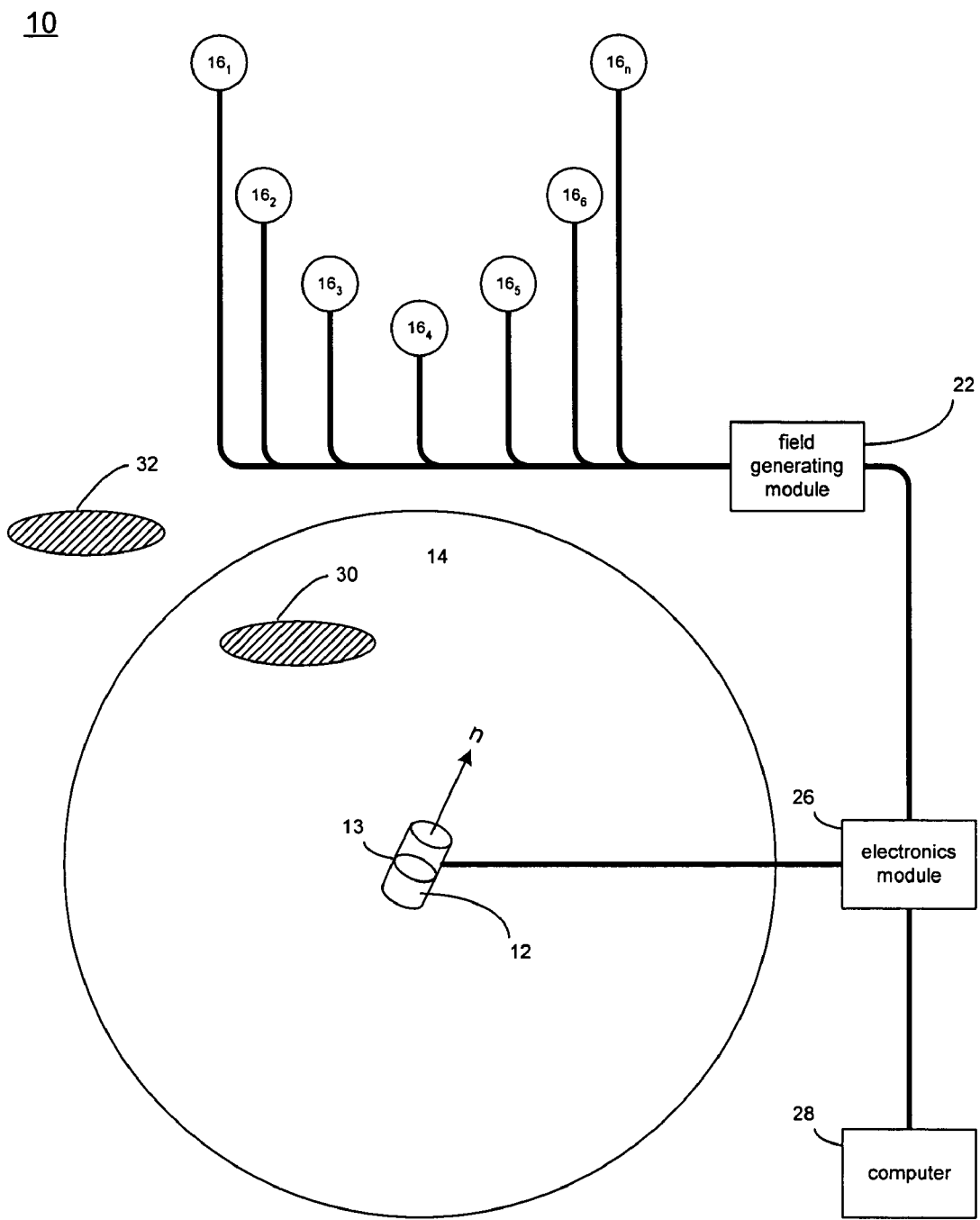
FIG. 1 is a schematic representation of a system that uses magnetic measurements to find a probe's system gain factor, location, and orientation.
Figure 2:
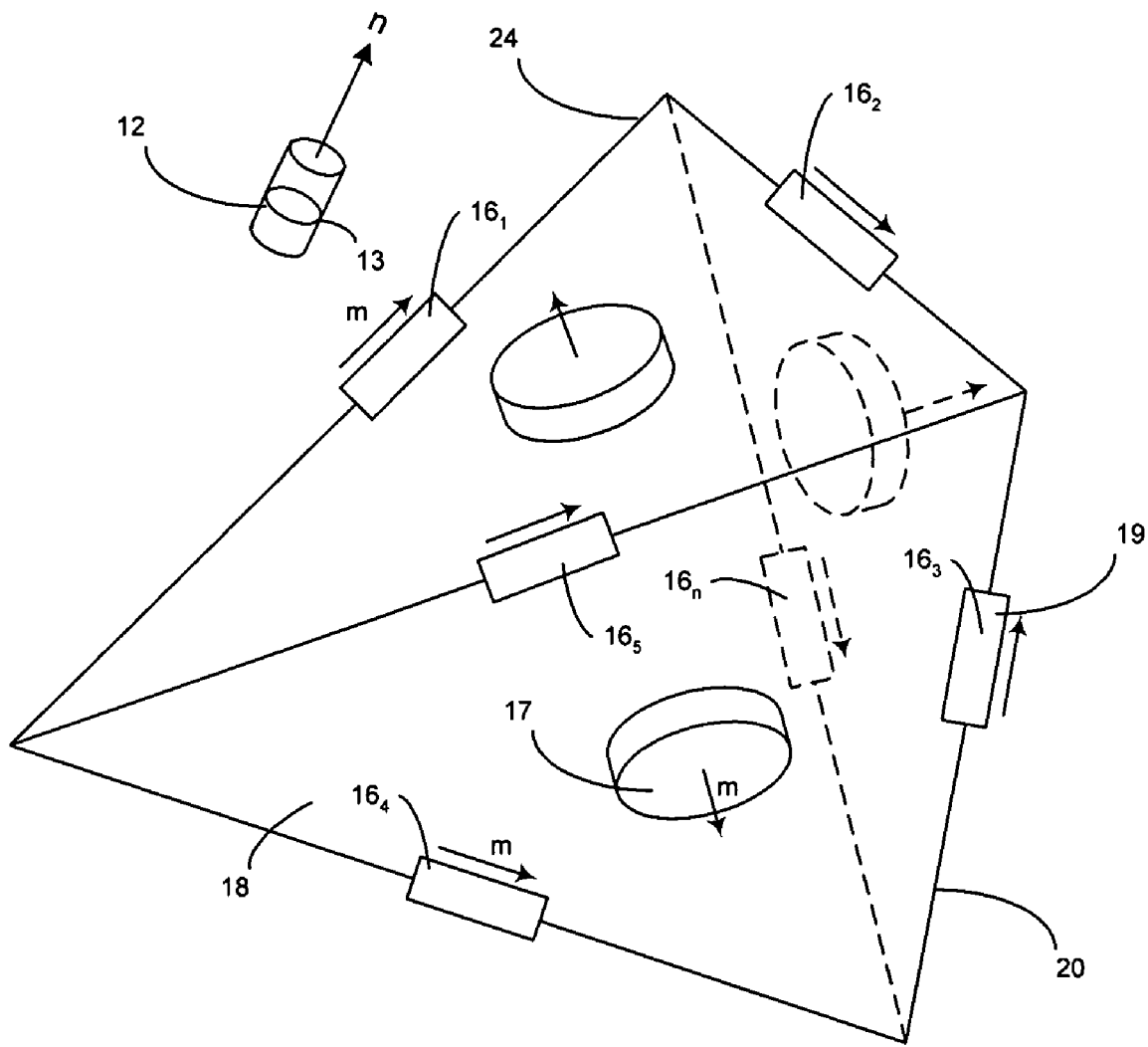
FIG. 2 is a perspective view of the system of FIG. 1.

Referring to FIGS. 1 and 2, there is shown a schematic representation of a system 10 that uses measurements of magnetic fields to find the location, orientation and system gain factor of a moveable probe 12. The moveable probe 12 is located inside a volume 14 (e.g., a body of a medical patient). System 10 also includes a plurality of field sources $16_{1-n}$ (e.g., small induction coils) that are located outside of volume 14. Field sources $16_{1-n}$ are driven by a field-generating module 22 (e.g., an alternating or direct current source). Please note that while seven field sources are shown, this is for illustrative purposes only and is not intended to be a limitation of the invention.

FIG. 2 is a side view of system 10 that shows the three-dimensional orientation and location of field sources $16_{1-n}$ and probe 12. Each field source $16_{1-n}$ is either: a surface-mount field source 17 located on a surface 18 of a regular tetrahedron 24; or an edge-mount field source 19 located on an edge 20 of a regular tetrahedron 24. The field sources $16_{1-n}$ are typically oriented so that their internal magnetic moments "m" are either perpendicular to the surfaces 18 of tetrahedron 24 or parallel to the edges 20 of tetrahedron 24. Probe 12 is located outside of tetrahedron 24 and has an orientation defined by a normal direction "n" to a sensor 13 that measures local magnetic field values. Sensor 13 may include a simple coil, several coils, a Hall sensor, or a flux gate sensor and may measure a magnetic field flux or magnetic field differential. Note that while system 10 is shown to include a single tetrahedron 24 having a maximum of four surface-mount field sources 17 and six edge-mount field sources 19, this is for illustrative purposes only and is not intended to be a limitation of the invention, as the positioning of these field sources $16_{1-n}$ can be adjusted and reconfigured as known by those skilled in the art. For example, a pair of tetrahedrons 24 utilizing only edge-mount field sources 19 can be utilized. This configuration allows for a maximum of twelve distinct field sources.

Each source $16_{1-n}$ may also include single or multiple field coils. For a source $16_{1-n}$ with a single coil, the magnetic field in the volume 14 can be approximated by a dipole field. For a source $16_{1-n}$ with several coils, the magnetic field in the volume 14 may be a higher multipole field. In one embodiment, each source $16_{1-n}$ uses two identical coils whose normal vectors are anti-parallel. Such a source produces a magnetic quadrapole field in volume 14. A quadrapole field has larger spatial variations than a dipole field and thus, may be more convenient for locating probe 12.

Other embodiments may use field sources $16_{1-n}$ that primarily generate higher magnetic multipole fields. Further, other embodiments may use a different numbers of field sources $16_{1-n}$ or locate and orient the field sources $16_{1-n}$ differently.

Referring to FIGS. 1 and 2, magnetic fields from sources $16_{1-n}$ induce electromotive forces (EMF's) in internal sensor coil 13 of probe 12. An electronics module 26 connected to probe 12 measures the EMF's. The measured EMF's represent the measured local values of magnetic fields at the probe's location and orientation in space 14. Electronics module 26 also can identify the individual source $16_{1-n}$ that produces each measured EMF.

In one embodiment, measurement timing information is used to identify the source $16_{1-n}$ producing a measured field. In this embodiment, field-generating module 22 temporally multiplexes power to the different field sources $16_{1-n}$ and relays timing information to the electronics module 26.

In another embodiment, the field generating module 22 drives each field source $16_{1-n}$ at a different frequency. To identify the particular source $16_{1-n}$ of a measured field, electronics module 26 or computer 28 decomposes measured EMF's from the probe's coil 13 into frequency components. These frequency components of the measured fields are then matched to individual field sources $16_{1-n}$.

In either embodiment, electronics module 26 outputs several measured magnetic fields $B_{1-n}^{measured}$ corresponding to the individual field measurements performed. It is important to note that there are several hardware configurations that can generate these field measurements. For example, if eight distinct field measurements are desired, system 10 can be configured so that eight field sources $16_{1-n}$ are utilized in conjunction with a probe 12 incorporating one sensor coil 13. In this configuration sensor coil 13 would measure the field generated by each of the eight field sources $16_{1-n}$, resulting in eight distinct field measurements.

Alternatively, a probe 12 could be constructed that incorporates multiple sensor coils 13. For example, if a probe 12 was constructed that includes two sensor coils 13 (configuration not shown), this configuration would double the number of individual field measurements achievable by that probe (using the equivalent number of field sources $16_{1-n}$). Specifically, if probe 12 includes two sensor coils 13, each coil could independently measure the strength of the magnetic field generated by a single field source. Therefore, if (as stated above) eight distinct field measurements are desired and a probe 12 is utilized that includes two sensor coils 13, only four field sources $16_{1-n}$ would be required, as each coil 13 could independently measure the field generated by each of the four field sources, thus resulting in eight distinct field measurements.

These measured magnetic field values $B_{1-n}^{measured}$ depend on the system gain factor of probe 12 and the three-dimensional location and the orientation of the probe's coil 13. Please note that the lower case "n" is used to denote the number of measured magnetic fields (except where it denotes normal vectors in the various figures).

As stated above, the number of field sources $16_{1-n}$ and sensor coils 13 incorporated into and utilized by system 10 varies depending on the number of factors to be determined by the system. Specifically, system 10 will determine the system gain factor of probe 12. Additionally, system 10 will also determine the position and orientation of probe 12. As the position and orientation of probe 12 is described by specifying up to six degrees of freedom (i.e., x-axis position, y-axis position, z-axis position, roll, pitch, and yaw) for probe 12, the maximum number of position factors that system 10 will calculate is six. Therefore, the maximum number of factors (both positional and gain) that system 10 calculates is seven. Thus, the number of distinct field measurements required to determine these factors is one greater than the number of factors being determined. Accordingly, if system 10 is determining the system gain factor plus six positional factors (i.e., degrees of freedom), a total of seven calculated factors need to be determined. This would require eight distinct field measurements. As stated above, this can be achieved utilizing a probe 12 incorporating a single sensor coil 13 and eight field sources $16_{1-n}$. Alternatively, this could be achieved by utilizing a probe 12 incorporating eight sensor coils 13 (if physically possible) and only one field source $16_{1-n}$. Accordingly, the important issue is the number of distinct field measurements made and not the specific number of field source $16_{1-n}$ or sensor coils 13 employed.

Similarly, if system 10 is determining the system gain factor plus five positional factors (i.e., five degrees of freedom), a total of six calculated factors need to be determined. Again, as above, this can be accomplished utilizing a variety of configurations.

As will be described below, the use of a number of distinct field measurements that is greater than the number of factors being calculated allows for the determination of the quality of the guesses used during an iterative process. If this quality determination is not required (or desired), the specific number of distinct field measurement required would be equal to the number of factors being calculated.

Further, when employing multiple field sensors, it is important to realize that there is a gain factor associated with each sensor. Accordingly, for the example stated above concerning the determination of six degrees of freedom, since at least two non-coaxial sensor coils are required to determine six degrees of freedom, there are at least two system gain factors (one for each sensor coil). Therefore, when calculating the six degrees of freedom and system gain factor of a probe utilizing two non-coaxial sensor coils, the system gain factor actually consists of two components, namely a gain factor for each sensor within the probe. Accordingly, the total number of calculated factors is eight (six positional, the gain factor for the first field sensor, and the gain factor for the second field sensor) and, therefore, the number of distinct field measurements required is nine (if the quality determination is required or desired).

Electronics module 26 sends the measured field values to computer 28. Computer 28 uses the measured magnetic field values to determine the probe's system gain factor and location/orientation by comparing the measured magnetic field values to magnetic field values from a physical model, as will be described below in greater detail.

The physical model is a set of physical equations that determine values of magnetic fluxes measured by probe 12 as a function of several parameters. The parameters include: the position, orientation, and magnetic moments of field sources $16_{1-n}$; the location, orientation, and sensitivity of probe 12; and characteristics of electronics module 26. A vector (x, y, z) and a pair of angles ($\phi$, $\theta$) specify the three-dimensional location and orientation of sensor coil 13 of probe 12. If the probe 12 has multiple non-colinear coils, the parameters may include an additional angular parameter ($\psi$) that defines a rotational aspect of the probe 12. Note that this factor (i.e., the sixth degree of freedom) can only be calculated by utilizing a probe having a second coil on a different axis (non-coaxial), as multiple coils about the same axis would not allow system 10 to sense probe rotation about that axis.

As is known by those skilled in the art, the physical model may describe each source as a magnetic multipole so that the fields measured by sensor coil 13 are the associated multipole fields (e.g., dipole or quadrapole). The multipole field values depend on the system gain and the location, orientation, and magnetic moment "m" of each source $16_{1-n}$. The measured values of the magnetic flux depend on the location, size, orientation and gain of sensor coil 13 with respect to field sources $16_{1-n}$.

The physical model is also based on underlying assumptions about the environment near the volume 14. For example, the model assumes preselected values for the location and orientation of each field source $16_{1-n}$ and the absence of other sources or field distorting objects. The presence of field distorting objects 30, 32 (e.g., conductors or new field sources) may invalidate the model's predictions for field values. However, the negative effects of constant background fields are eliminated, as sensing coil 13 only measures time varying magnetic fields. Alternatively, if static field measurements are desired, a flux gate sensor or hall effect sensor (as is known in the art) can be utilized, as they allow for measurement of static (or constant) magnetic fields.

Figure 3:
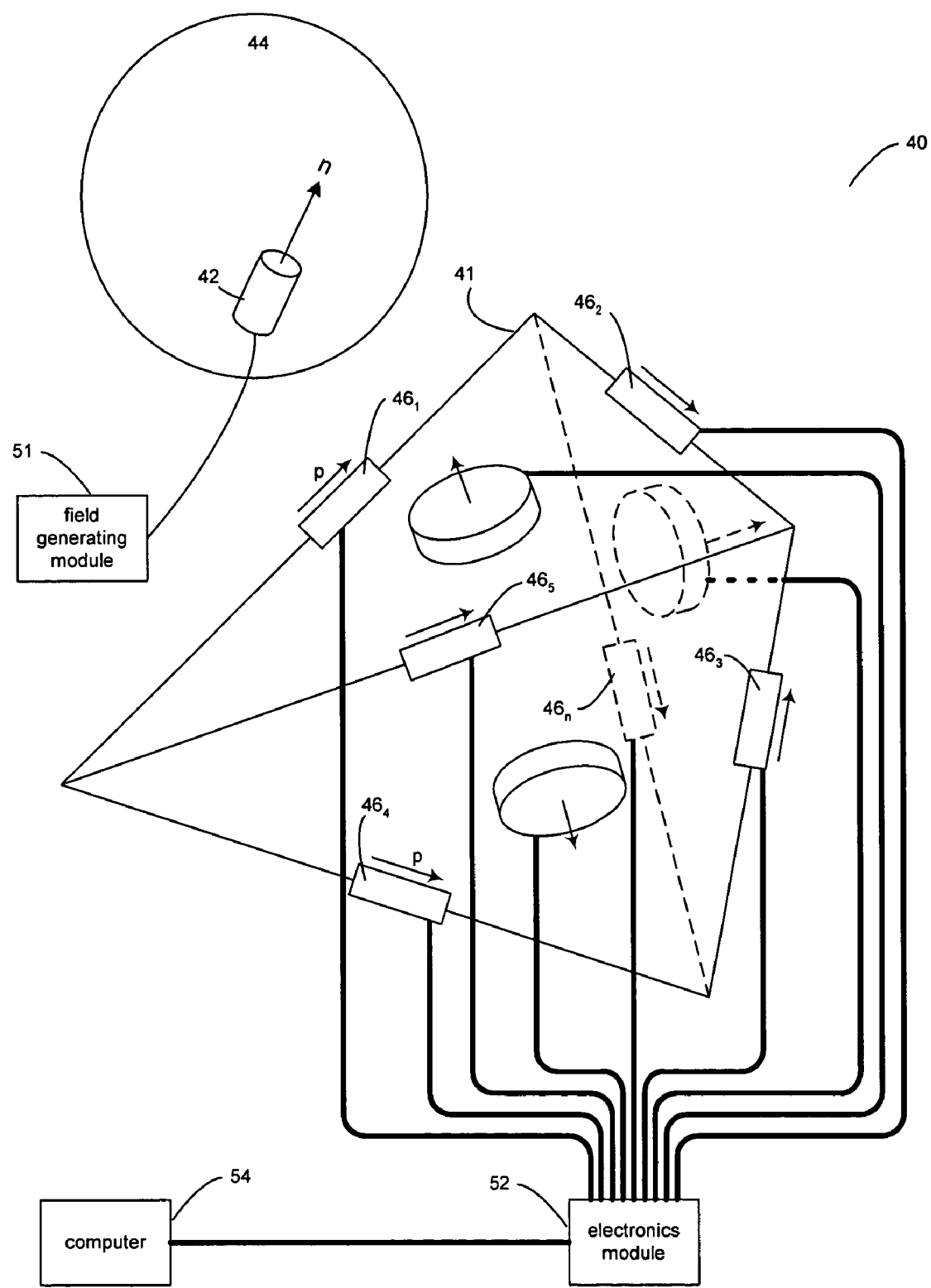
FIG. 3 is a side view of an alternate system that uses magnetic measurements to find a probe's gain, location, and orientation.

FIG. 3 shows another system 40 that uses magnetic measurements to find the system gain factor and location/orientation of a moveable probe 42. In system 40, the roles of the field sensors and sources are interchanged. The movable probe 42, which is located inside an observation volume 44, is a source of a magnetic field and external field sensors $46_{1-n}$ measure the magnetic field produced by probe 42. Probe 42 connects to a field-generating module 51 (e.g., a voltage source). As above, these field sensors $16_{1-n}$, which are located on either the edges or surfaces of a tetrahedron 41, measure either magnetic fields or magnetic field gradients through induced EMF's. Each sensor $46_{1-n}$ may have one or more magnetic field sensors oriented to measure fields in various directions. Each sensor $46_{1-n}$ has an orientation "p" fixed by the orientation of its one or more internal magnetic field sensors.

Please note that, as stated above, the location and orientation of each sensor, as well as the number of sensors $46_{1-n}$ utilized, may vary depending on the specific application and the number of factors (i.e., position/orientation and system gain) being determined.

An electronics module 52 monitors EMF's from the various field sensors $46_{1-n}$ to determine the individual magnetic field values. These measured magnetic field values are then sent to a computer 54, which calculates the system gain factor and location/orientation of the probe 42 from these measured magnetic field values.

Referring to FIGS. 1–3, both systems 10, 40 measure a set of magnetic fluxes to obtain a set of measured magnetic field values $B_{1-n}^{measured}$, such that "n" is greater than the number of factors (i.e., position and system gain) being calculated.

This set of measured field values $B_{1-n}^{measured}$, which are obtained from measured magnetic fluxes, also has a nonlinear dependence on the three-dimensional location/orientation of the probe and a linear dependence on the system gain factor. As stated above, the probe's location and orientation are defined by a vector (x, y, z) and at least a pair of azimuthal and polar angles ($\phi$, $\theta$), respectively. Further, the system gain factor of probe 12 is defined by a gain coefficient (g). By using a physical model for the "measured" field dependencies, the systems 10, 40 can iteratively determine the probe's gain factor, location, and orientation from the associated set of measured field values $B_{1-n}^{measured}$.

The physical model describes a preselected magnetic environment in the region of the field sensor[s] (i.e., the volumes 14 and 44 shown in FIGS. 1 and 3 respectively). The preselected magnetic environment may or may not include contributions from nearby conducting objects (i.e., objects 30 and 32). If the preselected environment is different from the actual environment, the model may predict incorrect magnetic field values; otherwise the predictions are correct. The actual environment may be different due to the presence of field distorting objects 30, 32. Field distorting objects 30, 32 include conducting objects that support eddy currents (e.g., a pair of surgical scissors, ferromagnetic materials, and active sources of magnetic fields). The presence of such objects can invalidate magnetic determinations of the probe's gain, location, and orientation.

The iterative process may also yield incorrect probe gain, location, and orientation because of hardware or software failures in modules 22, 26, 51, 52 or computers 28, 54.

The presence of distorting conditions may not be evident to users of systems 10, 40. The users may be unskilled with respect to physical basis for the magnetic location systems (e.g., the users may be medical doctors). To avoid errors by unskilled users, each system 10, 40 detects and warns users about the presence of potentially measurement distorting conditions (e.g., by flashing messages on a video monitor or through audio alert signals).

Please note that while probe 12, 42 is stated as being a probe, this is only intended to ease in the explanation of the subject invention and is for illustrative purposes only. Probe 12 can be various other devices known in the art (e.g., a catheter, an endoscope, biopsy needles, body-mounted position sensors, etc.).

Figure 4:
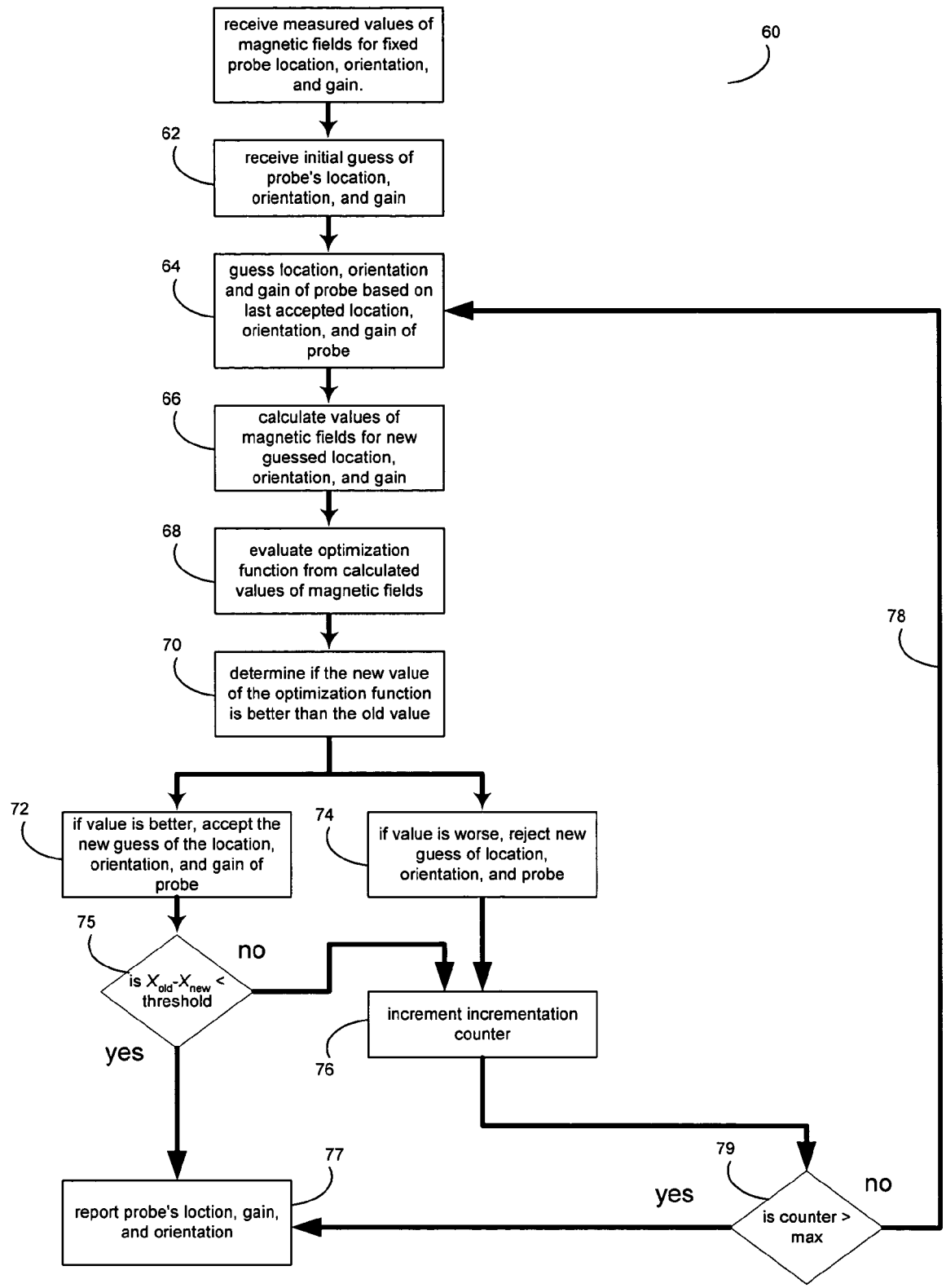
FIG. 4 is a flow chart for a process that iteratively guesses the gain, location, and orientation of a probe from measured magnetic field values.

FIG. 4 shows a flow chart for an iterative process 60 that uses the measured magnetic field values $B16_{1-n}^{measured}$ to determine the gain, location, and orientation of either probe 12 of FIGS. 1–2 or probe 42 of FIG. 3.

Process 60 receives 62 an initial guess for the probe's system gain factor, location and orientation. This initial guess can be predefined in the process, user definable, or randomly selected. The initial guess is a preselected point of the (x, y, z, $\phi$, $\theta$) parameter space that defines the location and orientation of the probe and a preselected system gain factor (g). The initial guess is the first accepted guess for the probe's gain, location, and orientation. From the last accepted guess, the process makes a new guess 64 for the probe's location, orientation, and gain. Naturally, while the initial preselected point (x, y, z, $\phi$, $\theta$) is shown to include five degrees of freedom, this is for illustrative purposes only and is not intended to be a limitation of the invention. Specifically, if greater or fewer degrees of freedom are desired, the preselected point (x, y, z, $\phi$, $\theta$) will have greater or fewer variables respectively.

Each new guess of the probe's gain, location, and orientation is found from the last accepted guess by any of a variety of procedures including the Levenberg-Marquardt process, a log-likelihood function, a neural network, simulated annealing, a genetic algorithm, a simplex process, or other processes known to those skilled in the art The Levenberg-Marquardt process is an iterative process used to find a best match between a set of measurements and a set of values obtained from preselected nonlinear model equations. The Levenberg-Marquardt process is described in: *Numerical Recipes in C: the Art of Scientific Computing*, by W.H. Press et al., Cambridge University Press 1992 and is incorporated herein by reference.

In Levenberg-Marquardt process, the model equations are the set of physical equations $B_{1-n}^{predicted}$ (x, y, $\phi$, $\theta$, g), which define the magnetic field values $B_{1-n}^{predicted}$ in terms of the probe's location, orientation, and gain (x, y, z, $\phi$, $\theta$, g). The model equations come from the physical laws of electrodynamics. In one embodiment, the model equations may describe the magnetic field of each field source as a magnetic dipole or as a magnetic quadrupole.

The Levenberg-Marquardt procedure iteratively tries to find a best match between the measured magnetic field values $B_{1-n}^{measured}$ and the magnetic field values $B_{1-n}^{predicted}$ predicted from the physical model equations. The Nth accepted guess for a match is associated with the probe gain, location, and orientation coordinates ($x_N$, $y_N$, $z_N$, $\phi_N$, $\theta_N$, $g_N$). From these coordinates and the physical model equations, the Levenberg-Marquardt process generates an $(N+1)^{th}$ guess that specifies the associated gain, location, and orientation coordinates ($x_{N+}$, $y_{N+1}$, $z_{N+1}$; $\phi_{N+1}$, $\theta_{N+1}$, $g_{N+1}$) of the probe. The Levenberg-Marquardt equation for the $(N+1)^{th}$ guess utilizes the values of the fields $B_{1-n}^{predicted}$ and derivatives of the fields $B_{1-n}^{predicted}$ evaluated at the value of the $N^{th}$ accepted guess for a match. The Levenberg-Marquardt process provides new guesses that rapidly produce the best match between measured field values $B_{1-n}^{measured}$ and predicted field values $B_{1-n}^{predicted}$ which are obtained from the non-linear model equations. Please note that the lower case "n" is used to denote the number of measured magnetic fields (e.g., $B_{1-n}^{measured}$) and the upper case "N" is used to denote the specific guess processed by the Levenberg-Marquardt procedure (e.g., $(N+1^{th})$).

The process 60 evaluates the quality of each new guess for the probe's gain, location, and orientation. To determine the quality of this guess, process 60 calculates 66 new magnetic field values which correspond to the new guess for the probe gain, location and orientation (i.e., $B_{1-n}^{predicted\ (new)}$ = $B_{1-n}^{predicted}(x_{N+1}, y_{N+1}, z_{N+1}; \phi_{N+1}, \theta_{N+1}, g_{N+1})$ for the $(N+1)^{th}$ guess. Using both the calculated (i.e., $B_{1-n}^{predicted}$) and the measured (i.e., $B_{1-n}^{measured}$) magnetic field values, process 60 evaluates 68 an optimization function. The optimization function is also referred to as an error function, because the optimization function is sensitive to differences between measured (i.e., $B_{1-n}^{measured}$) and calculated (i.e., $B_{1-n}^{predicted}$) field values. A global extremum of the optimization function defines the "best" guess for the location and orientation of the probe.

One embodiment uses a least-squares sum (i.e., $\chi^2$) as the optimization function. In general, these functions have both minima and maxima extrema. However, the extrema of the least-squares sum that we are interested in are the minima. The value of the least-squares sum $\chi^2(N)$ for the magnetic field associated with the $N^{th}$ guess has the form:

$$\chi^2(N) = \Sigma_{1-n}[B_{1-n}^{measured} - B_{1-n}^{predicted})x_N, y_N, \phi_N, \theta_N, g_N)]^2/\sigma_{1-n}^2.$$

The sum goes over the "1-n" members in the set of measured field values (i.e., $B_{1-n}^{measured}$) that are obtained for a single probe location and orientation. The term $\sigma_{1-n}$ represents uncertainties associated with the measurement of $B_{1-n}^{measured}$.

Process 60 determines 70 whether the value of the optimization function for the new guess is closer to a value at an extremum than the value for the last accepted guess. For the least-squares sum, since the extrema are minima, the new value is closer to a minimum if $\chi^2(N+1) < \chi^2(N)$. If the value of the optimization function for the new guess is closer to an extremum, process 60 accepts 72 the new guess for the gain, location, and orientation of the probe. If the value of the optimization function for the new guess is farther from an extremum (e.g., $\chi^2(N+1) > \chi^2(N)$), process 60 rejects 74 the new guess. After accepting 72 the new guess, process 60 determines 75 if the difference between the optimization function for the old and new guesses is less than an acceptable threshold (e.g., 0.01). If it is less than this threshold, the probe's gain, location, and orientation are reported 77. If the new guess is rejected 74 or if the difference between the optimization function for the old and new guesses is not less than an acceptable threshold, process 60 increments 76 a counter for the number of iterations performed. Process 60 then checks 79 to see if the incrementation counter is greater than the maximum number of iterations specified. If it is, process 60 then reports 77 the probe's gain, location, and orientation. If the number of iterations performed is not greater than the maximum number of iterations specified, process 60 loops back 78 to find a new and better guess of the probe's gain, location, and orientation.

Process 60 outputs the last accepted guess for the probe's gain, location, and orientation and a count specifying the number of iterations performed. In some embodiments, process 60 performs a preselected number of iterative loops 78 to find a better guess before reporting the accepted guess for the probe's gain, location, and orientation. This produces reported guesses that are closer to values associated with extremum of the optimization function.

Figure 5:
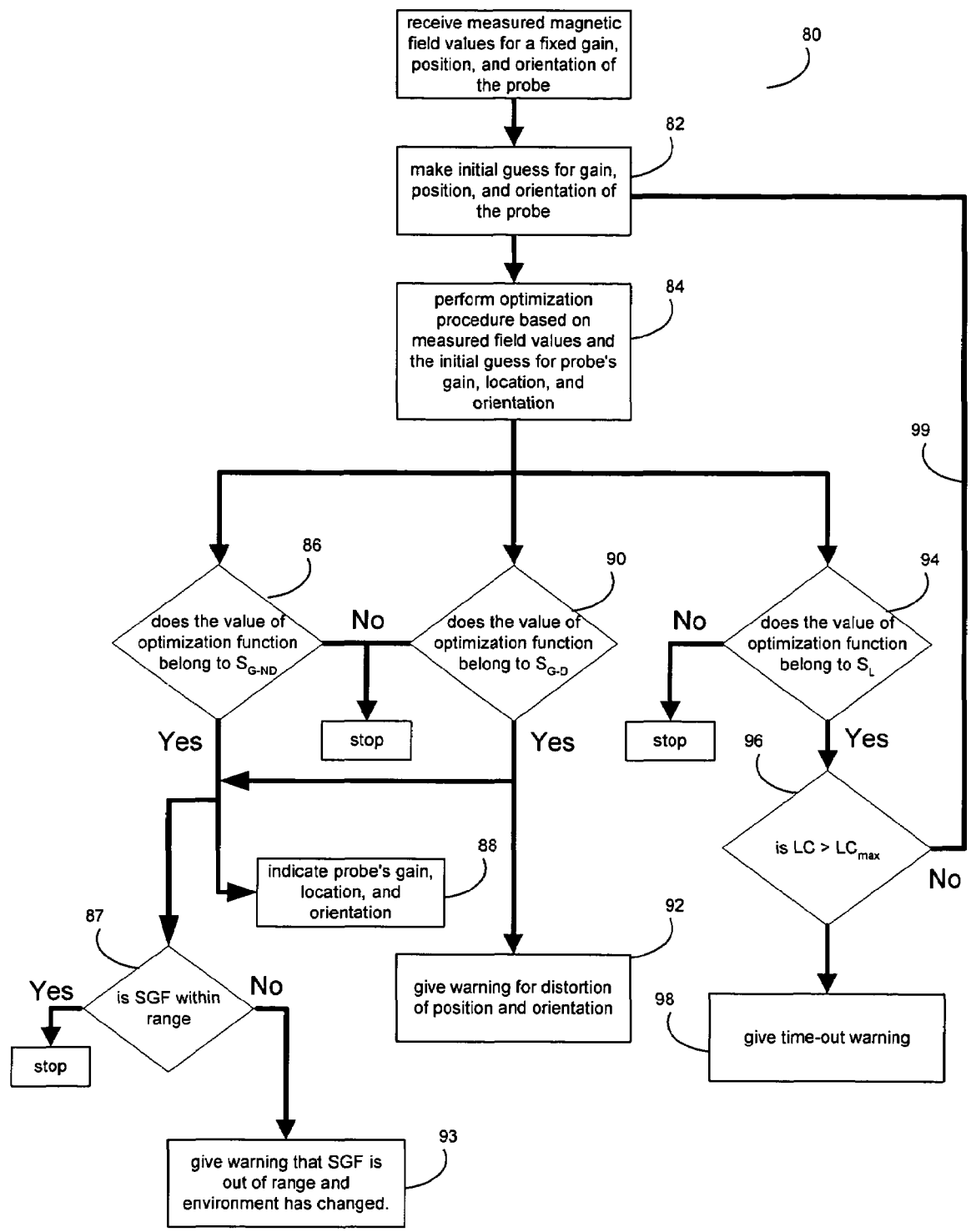
FIG. 5 is a flow chart for a process that determines whether the best guess of the gain, location, and orientation of a probe is reliable.

FIG. 5 is a flow chart for a process 80 that uses magnetic field measurements to determine a probe's gain, location, and orientation. Process 80 provides an initial guess 82 for the probe's gain, location, and orientation. The initial guess of the probe's gain, location, and orientation (x, y, z, $\phi$, $\theta$, g) may include either a preselected fixed point or a randomly selected point in the (x, y, z, $\phi$, $\theta$) space. For the selected initial guess, process 80 performs 84 iterative process 60 (of FIG. 4) to obtain a better guess for the probe's gain, location, and orientation. The better guess is based on the selected initial guess and the measured magnetic field values. Process 80 may perform several iterative loops of process 60 to obtain a better guess, which is closer to an extremum of the optimization function used in process 60. The optimization process 60 provides a value for the optimization function (e.g., the $\chi^2$ function) and the loop count (which indicates the number of iterations performed to obtain the better guess).

The value of the optimization function provides data indicative of the reliability of the better guess of the probe's gain, location, and orientation. Random measurement errors cause the value of the optimization function to fall on a probabilistic distribution function whose form is independent of the physical model for the magnetic field measurements. For the least-squares sum, the probabilistic distribution function is known as the $\chi^2$-distribution. Systematic measurement errors also affect the value of the optimization function.

The extrema of the optimization function can be maxima or minima and can fall into several classes. An extremum may be local or global extremum. Local and global extrema are distinguished by the associated values of the optimization function. For the least-squares sum, the value of the optimization function at a global minimum is smaller than the value of the function at a local minimum. Thus, global and local minima are associated with respective low and high values of the least-squares sum.

An extremum may also correspond to a situation in which measurements of magnetic fields are either distorted or undistorted. For the least squares sum, values of the optimization function at global minima for undistorted measurements are smaller than values of the optimization function at global minima for distorted measurements. Also, values of the optimization function at global minima for distorted measurements are smaller than values of the optimization function at local minima.

Thus, values of the optimization function at extrema carry information about the quality of the estimates of a probe's gain, location, and orientation obtained through process 60. The information enables determining whether random or systematic errors are present. Values of the least-squares sum at extrema are typically ordered. The lowest values correspond to global minima in the absence of distortions to field measurements. Intermediate values correspond to global minima in the presence of distortions to field measurements. The highest values correspond to false or local minima for which estimates of the probe's gain, location, and position are not reliable.

Distortions may occur during generation of magnetic fields, measurement of magnetic fields, acquisition of field measurements, or processing of field measurements. The distortions to the generation of magnetic fields may occur due to a failure of a field source $16_{1-n}$, probe 42, or field-generating module 22 or 51. The distortion of magnetic field measurements may result from the presence of conductors or ferromagnetic materials in the monitored space, which distort the time-varying magnetic fields. Distortion during the acquisition or processing of magnetic field measurements may result from hardware or software failures (e.g., in electronics modules 26, 52 or computers 28, 54).

Prior to performing process 80, a calibration is performed to classify extrema of the optimization function. The calibration classifies extrema of the optimization function into three or more sets ($S_i$). One set ($S_{G-ND}$) corresponds to real global extrema of the optimization function for which field measurements and field measurement processing is not distorted. Another set ($S_L$) corresponds to false or local extrema of the optimization function. A third set ($S_{G-D}$) corresponds to real global extrema of the optimization function for which either field measurements or field measurement processing is distorted.

New sets may be formed from the sets ($S_{G-ND}$, $S_L$, and $S_{G-D}$) by set intersection and union operations. One set ($S_{ND}$) includes values of the optimization function that are only associated with extrema of the function for which field measurements and measurement processing are not distorted. This set ($S_{ND}$) is defined as $S_{G-ND}-(S_L \cup S_{G-D})$. Another set ($S_D$) includes values of the optimization function that are only associated with global extrema of the function for which field measurements or field measurement processing is distorted. This set ($S_D$) is defined as $S_{G-D}-(S_L \cup S_{G-ND})$. Another set ($S_{L0}$) includes values of the optimization function that are only associated with false or local extrema of the function. This set ($S_{L0}$) is defined as $S_L-(S_{G-ND} \cup S_{G-D})$. Finally, a set ($S_{ND-D}$) includes values of the optimization function that are only associated with global extrema of the function. For values in $S_{ND-D}$, the field measurements and field measurement processing may or may not be distorted. $S_{ND-D}$ is defined as $S_{G-ND} \cup S_{G-D}$. In various embodiments, some of the above-described sets ($S_i$) may be empty.

Referring again to FIG. 5, process 80 uses the calibrated classification of values of the optimization function to classify extrema found with iterative process 60. Process 80 determines 86 whether the value of the optimization function at each extremum corresponds only to a global minimum without distortion (i.e., whether the value belongs to $S_{G-ND}$). If the value belongs to set $S_{G-ND}$, process 80 registers 88 the associated "better" guess for the probe's gain, location, and orientation as the probe's gain, location, and orientation. For example, the "better" guess for the location/orientation coordinates and the gain (x, y, z, φ, θ, g) may be displayed on a computer screen for a user to view as the final estimate of the gain, location, and orientation of the probe. Further, process 80 determines 87 if the system gain factor is within an acceptable range. If so, process 80 stops. If not, process 80 provides 93 a warning to the user that the system gain factor is out of range and, therefore, the probe's operating environment has changed.

Additionally, process 80 determines 90 whether the value of the optimization function for the "better" guess corresponds to a global extremum in the presence of a distortion (i.e., whether the value belongs to $S_{G-D}$). If the value belongs to set $S_{G-D}$, process 80 provides 92 a warning to the user and also registers 88 the new guess for the probe's gain, location, and orientation for the viewer to see. For example, the warning may be an audio signal or a flashing signal on a computer display for a user to hear or view.

Further, process 80 also determines 94 whether the value of the optimization function corresponds to a local extremum (i.e., whether the value belongs to $S_L$). If the value belongs to $S_L$, process 80 determines 96 whether the loop count (LC) is greater than a preselected timeout value ($LC_{max}$). If $LC > LC_{max}$, process 80 generates 98 a timeout warning. If $LC \leq LC_{max}$, process 80 loops back 99 to generate a better new guess for the probe's gain, location, and orientation (i.e., process 80 ignores the current new guess). In the loop back 99, process 80 selects a new initial guess for the probe's gain, location, and orientation (e.g., by randomly selecting a new gain (g) and a new point (x, y, z, φ, θ) in the probe's coordinate space). Other processes for selecting the new initial guess so that the process 60 subsequently produces a better guess for a "global" extremum are known to persons of skill in the art.

In some embodiments, process 80 tries to obtain a better guess for the gain, location, and position of the probe after producing a warning that a distortion is present. For example, if the number of field measurements is greater than the number of parameters plus one, process 80 may produce a better guess by discarding one of the measured field values $B_{1-n}^{measured}$ and repeating process 80. If the distortion affects only the discarded field value, discarding the distorted value will produce a better estimate of the probe's gain, location, and orientation. One field measurement may be distorted because of the presence of a conductor near one field sensor or because of a hardware failure in one sensor.

Some embodiments of process 80 handle overlapping extrema values, which belong to more than one of the sets of $S_L$, $S_{G-ND}$, and $S_{G-D}$, differently. For extrema values in both $S_L$ and $S_{G-D}$, process 80 may provide 92 a warning, indicate 88 the guessed probe location and orientation, and try to find a non-overlapping extrema value by repeating steps 82 and 84 for a new initial guess of the probe's gain, location, and orientation. For extrema values belonging to the set $S_L - S_{L0}$, the process may generate a warning that identifies the extrema value as overlapping and then reselect an initial guess for the probe's gain, location, and orientation and re-execute process 60 to try to find a value not belonging to $S_L - S_{L0}$. Of course, overlapping subsets such as $S_L - S_{L0}$ may also be empty.

It is important to note that the system gain factor can also be used as a means for detecting measurement distortion. The basis for this is the assumption that the system gain factor should remain essentially constant and stay within a defined range (which is typically determined during system calibration). Deviations from this range are indicative of a change in the probe's environment or in the system itself. This system gain factor range (SGFR) has to be chosen so that it can accommodate normal system gain factor variations for different probe positions and orientations throughout the operating volume. This range may also take into account gain variations caused by manufacturing tolerances and environmental factors (e.g., temperature variations, the presence of conductive objects, etc.).

If uniform damping of the magnetic field(s) (as sensed by the magnetic field sensors) occurs due to the presence of conductive objects within the operating volume, this uniform damping is automatically compensated for when the system gain factor is determined. Further, this compensation occurs without any loss in the positional and/or orientation accuracy of the system.

Accordingly, this automated uniform damping compensation allows for the determination of the probe's position/orientation within metallic tubes (e.g., a biopsy needle with a field sensor in its stylet). This allows for the tracking of the tip of a biopsy needle as it travels through the human body. This is an important advantage, as biopsy needles tend to bend and/or flex when passing through the body and, accordingly, the tip's position cannot be accurately interpolated. These advantages extend to other metallic tube objects, such as endoscopes, brachytherapy applicators etc.

Figure 6:
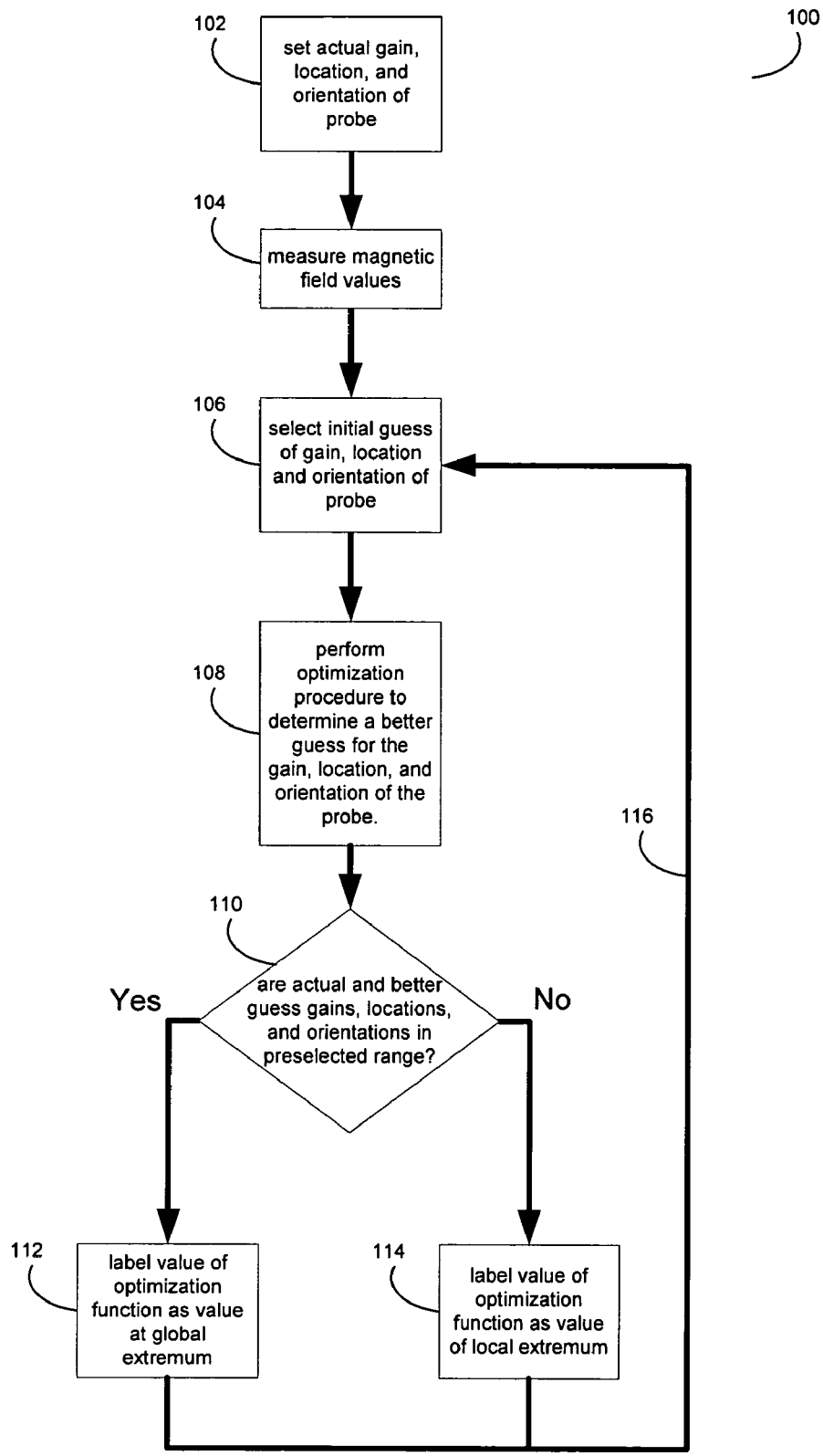
FIG. 6 is a flow chart for a process that evaluates an error or optimization function at global and local extrema.

The system can determine whether the probe is inside of a metallic tube by defining the SGFR such that system gain factor values for sensors within metallic tubes are not included in this range. FIG. 6 is a flow chart for a calibration process 100 that finds values of the optimization function at extrema to define the membership of sets $S_{G\text{-}ND}$ and $S_L$. If iterative process 60 (of FIG. 4) generates a real global extremum, the probe's gain, location, and orientation found by process 60 correlate closely to the actual gain, location, and orientation of the probe. If iterative process 60 generates a false or local extremum of the optimization function, the probe's gain, location, and orientation found by process 60 do not correlate closely to the actual gain, location, and orientation of the probe.

To perform this calibration, process 100 positions 102 the probe at a selected location and orientation. Further, an initial gain is selected for the probe. The initial gain is based on an accepted range of gain values for a properly functioning probe. During calibration, the probe mounts on a mechanical positioning frame (not shown) that positions the probe at the selected location and orientation. The mechanical positioning frame is made of materials that do not distort magnetic fields and provides a separate measurement of the selected actual location and orientation of the probe. The separate measurements may be optical measurements or mechanical measurements. Process 100 measures 104 the magnetic field values that correspond to the selected probe location and orientation.

Process 100 selects 106 an initial guess of the gain, location and position of the probe for optimization process 60. From the measured field values and the initial guess, process 100 performs 108 iterative optimization procedure 60 to obtain a better-guess value of the probe's gain, location and orientation. The optimization procedure 60 also provides a value for the optimization function that corresponds to the better guess for the probe gain, location and orientation and is a value of the optimization function at an extremum.

Process 100 compares 110 the better-guess and actual coordinates of the probe's gain, location and orientation to determine whether both coordinates are in close proximity to each other. The better guess $(x_N, y_N, z_N, \phi_N, \theta_N, g)$ and actual values $(x, y, z, \phi, \theta, g)$ of the probe coordinates are close if the values are within a preselected range of each other in a component-by-component fashion. If the better-guess and actual coordinates are close, the process 100 labels 112 the corresponding value of the optimization function as a value belonging to $S_{G\text{-}ND}$. If the better-guess and actual probe coordinates are not close, process 100 labels 114 the corresponding value of the optimization function as a value belonging to $S_L$.

To classify values of the optimization function at each extremum, process 100 loops back 116 and repeats steps 106-114 for other initial guesses of the probe's gain, location and orientation. These repetitions for different initial guesses cover the whole space $(x, y, z, \phi, \theta, g)$ of possible probe coordinates representatively (e.g., by randomly selecting points in the $(x, y, z, \phi, \theta, g)$ space).

Process 100 also repeats the classification of values of the optimization function at extrema for other selections of the actual probe gain, location and orientation. The repetitions for other actual probe gain, locations and orientations cover a representative portion of the parameter space $(x, y, z, \phi, \theta, g)$ representatively (e.g., with randomly selected points). The representative portion may be a portion of the entire space $(x, y, z, \phi, \theta, g)$ that is related to other portions of the space by symmetry rotations.

These repetitions may generate different extrema values of the optimization function that belong to $S_{G\text{-}ND}$ and/or $S_L$. For the least-squares sum, the optimization function has smaller values at global minima (i.e., in the presence or absence of measurement distortions) than at local minima.

Figure 7:
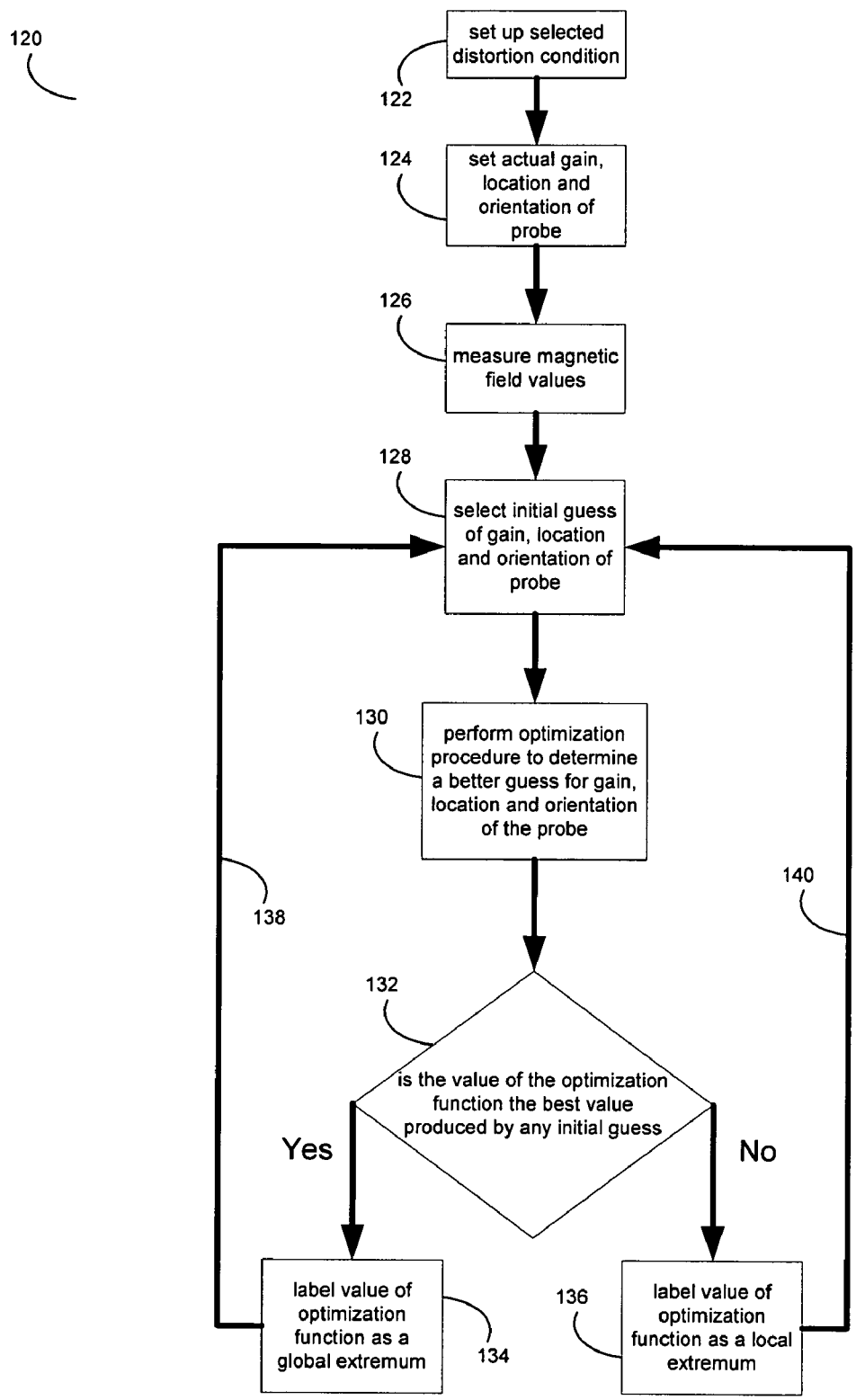
FIG. 7 is a flow chart for a process that determines extrema values of the error or optimization function that correspond to the presence of distortions.

FIG. 7 is a flow chart for a calibration process 120 that finds values of the optimization function belonging to $S_{G\text{-}D}$. The values of $S_{G\text{-}D}$ correspond to extrema of the optimization function that occur when distortions affect the iteration process 60 (of FIG. 4). Process 120 may be performed separately for each type of distortion that can affect either magnetic field measurements or the processing of magnetic field measurements. The distortions may result from nearby conducting or ferrous objects, nearby field sources, sensor hardware failures, field source hardware/software failures, and/or software measurement processing failures.

Process 120 physically sets up 122 a selected type of distortion for the system. For example, the setting up of a distortion may include placing a pair of conducting scissors inside the monitored volume or causing a hardware failure in the electronics module. After setting up the distortion condition, process 120 positions 124 the probe with the mechanical positioning frame and receives the value of the probe's actual location and orientation. Further, an initial gain is selected for the probe. The initial gain is based on an accepted range of gain values for a properly functioning probe. The process also measures 126 the magnetic field values that depend on the probe's actual gain, location and orientation. Process 120 also selects 128 an initial guess for the gain, location and orientation of the probe.

From the measured field values and selected initial guess, process 120 utilizes 130 the iterative process 60 to obtain a better guess for the probe's gain, location and orientation. Iterative process 60 returns an associated extrema value of the optimization function that corresponds to each better guess. Process 120 determines 132 whether the new value is better than other extrema values of the optimization function, which were generated from different initial guesses for the probe's gain, location and position. For the least-squares sum, the best extrema value is the minimum value.

If the new value is better than values associated with earlier accepted guesses, the process 120 labels 134 the new value as a value of the optimization function at a global extremum (i.e., as a member of $S_{G\text{-}D}$). Values of the optimization function that belong to $S_{G\text{-}D}$ indicate the presence of distortion. If the new value is not better than earlier values of the optimization function associated with accepted guesses, process 120 labels 136 the new value as a value that corresponds to a false or local extremum. After classifying the extrema value, process 120 loops back 138, 140 to repeat the search for values of the optimization function at other extrema by selecting a different initial guess for the probe's gain, location and orientation. The best extrema value for various initial guesses of the probe's gain, location and orientation provides a value in $S_{G\text{-}D}$.

The process also repeats the search for values of the optimization function in $S_{G\text{-}D}$ for different actual gains, locations and orientations of the probe. For each actual gain, orientation and location, an extrema value of the optimization function in $S_{G\text{-}D}$ may be generated. Similarly, different positions of a distorting object (e.g., objects 30 and 32 of FIG. 1) may generate different extrema values of the optimization function, which belong to $S_{G-D}$.

In some embodiments, the extrema values of the optimization function for different types of distortion are distinguishable. Distinguishable extrema values fall in different ranges. In such embodiments, calibration process 120 is performed separately for the different types of distortion to obtain ranges of extrema values of the optimization function for each separate type of distortion. Process 80 (of FIG. 5) uses the extrema values to classify the type of distortion, e.g., hardware failure, software failure, or nearby conducting object.

Figure 8:
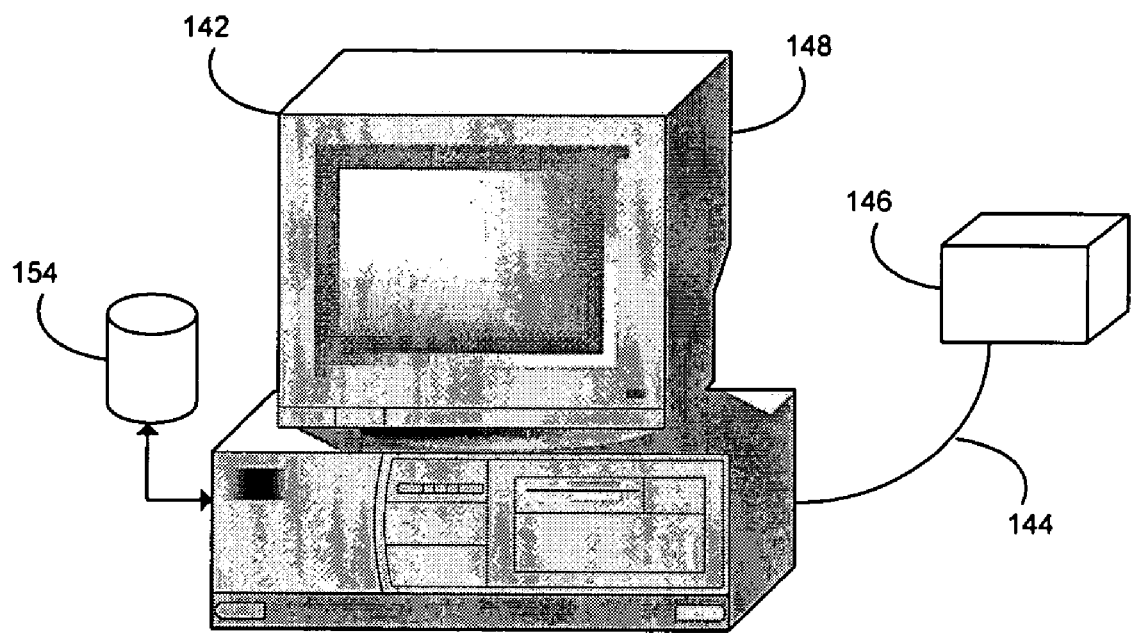
FIG. 8 shows a computer that finds a probe's gain, location, and orientation from measurements of magnetic fields.

FIG. 8 shows a computer 142 that determines the gain, location, and orientation of a probe from measurements of magnetic fields and indicates the presence of distortions to the determinations. Computer 142 may be an embodiment for computer 28 of FIG. 1 or computer 54 of FIG. 3.

Computer 142 receives data on measured magnetic field values from a line 144 that connects to an output of an electronics module 146. The module 146 may be module 26 (FIG. 1) or module 52 (FIG. 3). Computer 142 processes the data according to processes 60 (FIG. 4) and 80 (FIG. 5) to determine a probe's gain, location, and orientation and the presence or absence of distortion. Computer 142 displays the results of the determinations on a screen 148. Computer 142 has a data storage drive 154 (e.g., a hard disk or optical drive) for storing the above-described executable programs/processes and the data generated therefrom.

A number of embodiments of the invention have been described. Nevertheless, it will be understood that various modifications may be made without departing from the spirit and scope of the invention. Accordingly, other embodiments are within the scope of the following claims.

What is claimed is:

1. A system for determining the position, orientation and system gain factor of a probe comprising:
   a plurality of magnetic field sources;
   at least one magnetic field sensor, wherein a combination of a magnetic field sensor and a magnetic field source generates a unique measured magnetic field value;
   a probe whose gain, position, and orientation affects said unique measured magnetic field values; and
   a processor, configured to receive and iteratively process said unique measured magnetic field values, for determining a system gain factor indicative of the gain of said probe and a plurality of location factors indicative of the position and orientation of said probe, wherein said iterative process is configured to determine a function of the differences between said measured magnetic field values and a plurality of predicted magnetic field values.

2. The system for determining the position, orientation and system gain factor of claim 1 wherein the number of unique measured magnetic field values generated is at least equal to the sum of the number of gain and location factors calculated.

3. The system for determining the position, orientation and system gain factor of claim 2 wherein said processor includes a calculated location process for calculating said predicted magnetic field values, wherein said calculated location process guesses an initial gain, position, and orientation for said probe, and calculates said predicted magnetic field values based on a physical model and said initial gain, position, and orientation.

4. The system for determining the position, orientation and system gain factor of claim 3 wherein said initial position and orientation is a predetermined fixed point.

5. The system for determining the position, orientation and system gain factor of claim 3 wherein said initial position and orientation is a randomly selected fixed point.

6. The system for determining the position, orientation and system gain factor of claim 3 wherein said processor includes an optimization function for determining an extremum indicative of said differences between said measured magnetic field values and said predicted magnetic field values.

7. The system for determining the position, orientation and system gain factor of claim 6 wherein said optimization function is a least squares sum function.

8. The system for determining the position, orientation and system gain factor of claim 6 wherein said processor includes a repositioning process for adjusting said initial gain, position, and orientation of said probe in response to said extremum being in a predefined range of unacceptable values, which is indicative of an unacceptable level of difference between said measured magnetic field values and said plurality of predicted magnetic field values.

9. The system for determining the position, orientation and system gain factor of claim 1 wherein said location factors include spatial coordinates.

10. The system for determining the position, orientation and system gain factor of claim 1 wherein said location factors include spherical coordinates.

11. The system for determining the position, orientation and system gain factor of claim 1 wherein said location factors include rotational coordinates.

12. A system for determining the position, orientation and system gain factor of a probe comprising:
    one of a plurality of magnetic field sensors and a plurality of magnetic field sources;
    at least one of the other of the magnetic field sensors and magnetic field sources, wherein a combination of a magnetic field sensor and a magnetic field source generates a unique measured magnetic field value,
    a probe whose gain, position, and orientation affects said unique measured magnetic field values; and
    a processor, configured to receive and iteratively process said unique measured magnetic field values, for determining a system gain factor indicative of the gain of said probe and a plurality of location factors indicative of the position and orientation of said probe;
    wherein said iterative process is configured to determine a function of the differences between said measured magnetic field values and a plurality of predicted magnetic field values.

13. The system for determining the position, orientation and system gain factor of claim 12 wherein the number of unique measured magnetic field values generated is at least equal to the sum of the number of gain and location factors calculated.

14. The system for determining the position, orientation and system gain factor of claim 13 wherein said processor includes a calculated location process for calculating said predicted magnetic field values, wherein said calculated location process guesses an initial gain, position, and orientation for said probe, and calculates said predicted magnetic field values based on a physical model and said initial gain, position, and orientation.

15. The system for determining the position, orientation and system gain factor of claim 14 wherein said initial position and orientation is a predetermined fixed point.

16. The system for determining the position, orientation and system gain factor of claim 14 wherein said initial position and orientation is a randomly selected fixed point.

17. The system for determining the position, orientation and system gain factor of claim 14 wherein said processor includes an optimization function for determining an extremum indicative of said differences between said measured magnetic field values and said predicted magnetic field values.

18. The system for determining the position, orientation and system gain factor of claim 17 wherein said optimization function is a least squares sum function.

19. The system for determining the position, orientation and system gain factor of claim 17 wherein said processor includes a repositioning process for adjusting said initial gain, position, and orientation of said probe in response to said extremum being in a predefined range of unacceptable values, which is indicative of an unacceptable level of difference between said measured magnetic field values and said plurality of predicted magnetic field values.

20. The system for determining the position, orientation and system gain factor of claim 12 wherein said location factors include spatial coordinates.

21. The system for determining the position, orientation and system gain factor of claim 12 wherein said location factors include spherical coordinates.

22. The system for determining the position, orientation and system gain factor of claim 12 wherein said location factors include rotational coordinates.

* * * * *